United States Patent [19]
O'Lenick, Jr.

[11] Patent Number: 5,929,263
[45] Date of Patent: Jul. 27, 1999

[54] GUERBET BRANCHED QUATERNARY COMPOUNDS

[75] Inventor: Anthony J. O'Lenick, Jr., Lilburn, Ga.

[73] Assignee: Lambent Technologies Inc, Norcross, Ga.

[21] Appl. No.: 09/098,790

[22] Filed: Jun. 17, 1998

[51] Int. Cl.[6] .................................................. C07C 233/00
[52] U.S. Cl. ............................................. 554/52; 554/51
[58] Field of Search ........................................ 584/51, 52

[56] References Cited

U.S. PATENT DOCUMENTS 5,488,121   1/1996   O'Lenick .

*Primary Examiner*—Deborah D Carr

[57] ABSTRACT

The present invention deals with the composition of matter and the utilization of certain novel guerbet based quat compounds. These materials are useful in personal care applications.

11 Claims, No Drawings

GUERBET BRANCHED QUATERNARY COMPOUNDS

BACKGROUND OF THE INVENTION

1. Field of the Invention

The present invention deals with novel, surfactants, specifically quats, based upon highly branched guerbet acids. The term "quats" is a shorthand for quaternary compounds.

2. Description of the Art Practices

Guerbet alcohols have been known for many years. Over the years there have been a number of derivatives patented. These materials can be oxidized into acids, which are raw materials for the preparation of the specific complex esters of the present invention. They possess the critical regiospecific guerbet linkage which when placed into amidoamine compounds and quats derived therefrom result in unexpected improvements in both liquidity oxidative stability.

U.S. Pat. No. 5,488,121 to O'Lenick, incorporated herein by reference, discloses di-guerbet esters based upon the reaction product of both a guerbet acid and a guerbet alcohol. The guerbet acids of that invention are raw materials used in the preparation of the compounds of the present invention.

FIELD OF THE INVENTION

The present invention deals with novel cationic surfactants based upon a highly branched guerbet acid. The introduction of the guerbet branch into the quats of the present invention results in improved conditioning in personal care formulations as well as improved odor stability in the formulation and improved liquidity of the aqueous quat per se.

DESCRIPTION OF THE ART PRACTICES

Quats are known in the art. Variation of carbon chain lengths in amido quats has direct effect upon the surfactant properties of the quat. while quats based upon short chain fatty acids can be made, they are germicidal and irritating to the skin and eyes. They also lack conditioning effects on hair. The use of fatty acids having more that 12 carbon atoms to make quats result in quats which provide foam in aqueous systems, but have little or no conditioning effects. The selection of a oleyl quats gives some improved viscosity, but the compound undergoes a process of oxidative instability referred to as rancidity, producing low molecular weight aldehydes with mal odor. The availability of a liquid, oxidatively stable quat that can be used in personal care systems has been elusive prior to the compounds of the present invention.

The recent availability of guerbet acids and their reaction to make quats results in the preparation liquid stable quats, having outstanding emulsifying properties and are very acceptable for use in personal care applications.

None of the prior quats possess the critical guerbet moiety. Molecules of the current invention have the guerbet group in the quat.

THE INVENTION

This invention relates to the use of a guerbet acid to make an guerbet alkyl amidopropyl dialkyl quat, which has unique, unexpected properties in personal care applications. Specifically, the quats of the present invention provide a smooth feel on the skin, outstanding viscosity in anionic systems, and are surprisingly oxidatively stable in aqueous personal care formulations.

Another aspect of the present invention is the guerbet amidopropyl dialkyl amine intermediate useful as an intermediate in the preparation of the quat of the present invention and other surfactant derivatives.

The compounds of the current invention are quats derived from guerbet acid and conform to the following structure;

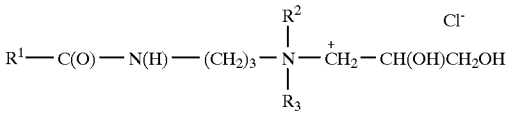

wherein:

$R^1$ is

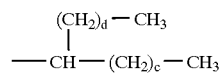

c and d are independently integers ranging from 3 to 17;

$R^2$ and $R^3$ are methyl or ethyl.

The presence of the —$CH_2$—$CH(OH)CH_2OH$ functionality on the nitrogen results in improved water solubility, and also provides improved humectancy and conditioning effects to the quaternary compound.

The quat is prepared in a two step reaction. The first step is the preparation of a guerbet amidoamine conforming to the following structure:

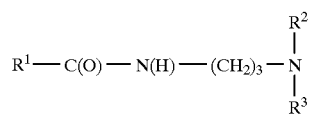

wherein:

$R^1$ is

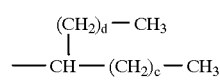

c and d are independently integers ranging from 3 to 17.

The reaction is as follows:

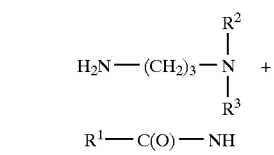

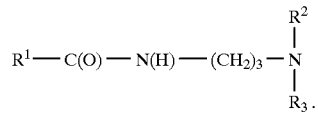

As previously stated another novel aspect of the present invention is the amidoamine intermediate conforming to the following structure:

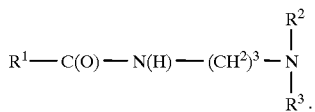

wherein:
R¹ is

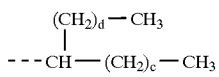

c and d are independently integers ranging from 3 to 17.

In the second reaction the amidoamine, prepared in the first reaction, is reacted in aqueous solution with of monochlorohydrin as follows:

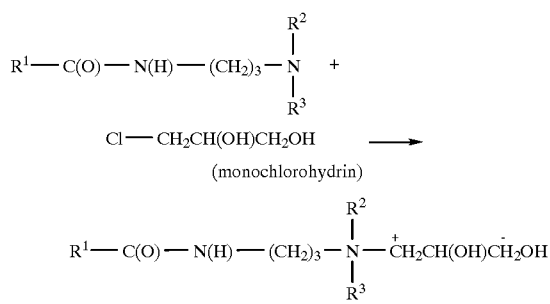

The concentration of the quat in water is generally between 20 and 50% with 35% being preferred. Glycols, lower alcohols and other polar solvents may also be added, if desired.

EXAMPLES

RAW MATERIALS

Guerbet Acids

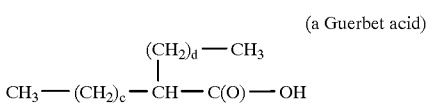

Vista Chemical practices the oxidation of guerbet alcohols commercially. The values of c and d were actually determined by analysis and are not dependant upon trade name for meaning.

| Example | Commercial Name | c | d |
|---|---|---|---|
| 1 | Isocarb 10 | 3 | 3 |
| 2 | Isocarb 12 | 4 | 4 |
| 3 | Isocarb 14 | 5 | 5 |
| 4 | Isocarb 16 | 6 | 6 |
| 5 | Isocarb 18 | 7 | 7 |
| 6 | Isocarb 20 | 8 | 8 |
| 7 | Isocarb 32 | 14 | 14 |
| 8 | Isocarb 40 | 17 | 17 |

Isocarb is a trademark of Vista.
Aminopropyl Amine
The compounds conform to the following structure:

Example 9

Dimethyl aminopropyl amine

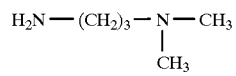

Example 10

Diethyl aminopropyl amine

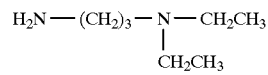

General Procedure

To the specified number of grams the specified dialkyl aminopropyl amine (Examples 9 and 10) is added the specified number of grams the specified guerbet acid (examples 1–9) under agitation. The temperature of the mass is raised to 180–200° C. and water is stripped off as formed. This temperature is held for between 1 and 12 hours. The acid value and the primary amine value drops to vanishingly small levels and tertiary amine level approaches theoretical.

The products are clear liquids and are liquid to temperatures.

| | Guerbet Acid | | Aminopropyl Amine | |
|---|---|---|---|---|
| Example | Example | Grams | Example | Grams |
| 11 | 1 | 171.0 | 9 | 122.0 |
| 12 | 2 | 199.0 | 9 | 122.0 |
| 13 | 3 | 227.0 | 9 | 122.0 |
| 14 | 4 | 255.0 | 9 | 122.0 |
| 15 | 5 | 283.0 | 9 | 122.0 |
| 16 | 6 | 311.0 | 9 | 122.0 |
| 17 | 7 | 479.0 | 9 | 122.0 |
| 18 | 8 | 592.0 | 9 | 122.0 |
| 19 | 1 | 171.0 | 10 | 150.0 |
| 20 | 2 | 199.0 | 10 | 150.0 |
| 21 | 3 | 227.0 | 10 | 150.0 |
| 22 | 4 | 255.0 | 10 | 150.0 |
| 23 | 5 | 283.0 | 10 | 150.0 |
| 24 | 6 | 311.0 | 10 | 150.0 |
| 25 | 7 | 479.0 | 10 | 150.0 |
| 26 | 8 | 592.0 | 10 | 150.0 |

The compounds are the intermediate conforming to the following structure:

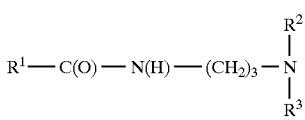

Monochlorohydrin is an item of commerce available from in Somerville, N.J. and conforms to the following structure

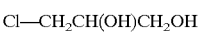

Ouat Synthesis

To 120.0 grams of monochlorohydrin is added to the specified amount of water. The solution is heated to 80° C. and the amidoamine (examples 11–26) is added under agitation. The pH is kept between 8–9 by adding NaOH as required. The reaction progress is monitored by the inorganic chloride level, which within 3–4 hours reaches theoretical.

Example 27

To 120.0 grams of monochlorohydrin is added 1,000 grams of water. The solution is heated to 80° C. and 438.0 293.0 grams of amidoamine (example 27) is added under agitation. The pH is kept between 8–9 by adding NaOH as required. The reaction progress is monitored by the inorganic chloride level, which within 3–4 hours reaches theoretical.

Examples 28–42

Example 27 is repeated, only this time the specified amount and type of amido amine is substituted for the amido amine of example 27.

|         | Amidoamine |       |
| ------- | ---------- | ----- |
| Example | Example    | Grams |
| 28      | 12         | 321.0 |
| 29      | 13         | 349.0 |
| 30      | 14         | 377.0 |
| 31      | 15         | 405.0 |
| 32      | 16         | 433.0 |
| 33      | 17         | 601.0 |
| 34      | 18         | 714.0 |
| 35      | 19         | 320.0 |
| 36      | 20         | 351.0 |
| 37      | 21         | 399.0 |
| 38      | 22         | 407.0 |
| 39      | 23         | 435.0 |
| 40      | 24         | 470.0 |
| 41      | 25         | 631.0 |
| 42      | 26         | 743.0 |

The products produced using the examples 27–42 are clear yellow viscous liquids. The products have outstanding oxidate stability and provide conditioning when applied to the hair. In addition they are not irritating to the skin or eye.

I claim:

1. A guerbet quat which conforms to the following structure:

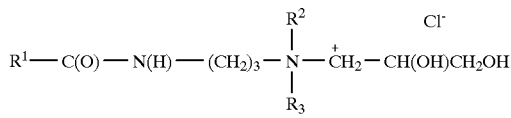

wherein:

$R^1$ is

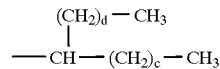

c and d are independently integers ranging from 3 to 17, $R^2$ and $R^3$ are methyl or ethyl.

2. A guerbet quat of claim 1 wherein $R^2$ is methyl.
3. A guerbet quat of claim 1 wherein $R^2$ is ethyl.
4. A guerbet quat of claim 1 wherein c is 3 and d is 3.
5. A guerbet quat of claim 1 wherein c is 4 and d is 4.
6. A guerbet quat of claim 1 wherein c is 5 and d is 5.
7. A guerbet quat of claim 1 wherein c is 6 and d is 6.
8. A guerbet quat of claim 1 wherein c is 7 and d is 7.
9. A guerbet quat of claim 1 wherein c is 8 and d is 8.
10. A guerbet quat of claim 1 wherein c is 14 and d is 14.
11. A guerbet quat of claim 1 wherein c is 17 and d is 17.

\* \* \* \* \*